(12) United States Patent
Niedermann et al.

(10) Patent No.: US 12,691,246 B2
(45) Date of Patent: Jul. 28, 2026

(54) PORTABLE AIR TREATMENT APPARATUS

(71) Applicant: Crane USA Inc., Itasca, IL (US)

(72) Inventors: Dirk Niedermann, Naples, FL (US);
Peter Joseph Zerillo, Chicago, IL (US)

(73) Assignee: Crane USA Inc., Itasca, IL (US)

( * ) Notice: Subject to any disclaimer, the term of this
patent is extended or adjusted under 35
U.S.C. 154(b) by 764 days.

(21) Appl. No.: 18/111,681

(22) Filed: Feb. 20, 2023

(65) Prior Publication Data

US 2024/0173513 A1     May 30, 2024

Related U.S. Application Data

(60) Provisional application No. 63/428,818, filed on Nov.
30, 2022.

(51) Int. Cl.
A61M 16/06 (2006.01)
A61H 33/12 (2006.01)
A61M 16/14 (2006.01)

(52) U.S. Cl.
CPC ............. A61M 16/14 (2013.01); A61H 33/12
(2013.01); A61M 16/06 (2013.01)

(58) Field of Classification Search
CPC ..................................................... A61H 33/12
See application file for complete search history.

(56) References Cited

U.S. PATENT DOCUMENTS

| | | | | |
|---|---|---|---|---|
| 3,712,307 A | * | 1/1973 | McLaughlin | A61H 33/12 |
| | | | | 4/537 |
| 2015/0209224 A1 | * | 7/2015 | Hsu | A61H 33/12 |
| | | | | 392/404 |
| 2017/0020781 A1 | * | 1/2017 | Tang | A61L 9/00 |

FOREIGN PATENT DOCUMENTS

| | | | | |
|---|---|---|---|---|
| WO | WO-2015165108 A1 | * | 11/2015 | A61H 33/12 |
| WO | WO-2015165115 A1 | * | 11/2015 | A61H 33/12 |

OTHER PUBLICATIONS https://www.youtube.com/watch?v=s2YDgV7NNbc, 2021.*
Vicks SinusInhaler: Personal Steam Inhaler Use and Care Manual,
2017.*

* cited by examiner

*Primary Examiner* — Bradley H Philips
(74) *Attorney, Agent, or Firm* — Wood, Phillips, Katz,
Clark, & Mortimer

(57) ABSTRACT

A portable air treatment apparatus made up of: a) an oper-
ating unit for generating fluid droplets to be entrained in air
and directed in a stream to an outlet for the operating unit;
b) a mask having a body extending around a volume and a
surface/edge at an outlet for the volume to be situated near
a user's frontal face region, with the mask and operating unit
configured so that the mask can be releasably operatively
connected to the operating unit whereby the stream of air
with entrained fluid droplets flows through the mask body
inlet and into the mask body volume; and c) at least one
additive component. The mask and at least one additive
component, when in an operative position, are movable as a
unit relative to the operating unit as the mask is separated
from the operating unit.

21 Claims, 15 Drawing Sheets

PORTABLE AIR TREATMENT APPARATUS

CROSS-REFERENCE TO RELATED APPLICATIONS

This is a non-provisional application claiming priority to U.S. Provisional Application No. 63/428,818, filed Nov. 30, 2022, which is incorporated herein by reference.

BACKGROUND OF THE INVENTION

Field of the Invention

This invention relates to air treatment apparatus that generate fluid droplets that are entrained in air to be inhaled by a user in the vicinity of the apparatus and, more particularly, to such an apparatus that utilizes an additive component that further treats the inhalable air.

Background Art

Many different portable air treatment apparatus are currently commercially available. One category of these apparatus utilizes a mask defining a volume from which treated air can be inhaled by a user. The mask volume has an outlet at which an edge is formed that generally conforms to the frontal face region of a user. The generated treated air is inhaled by the user preferably with the user's frontal face region spaced slightly away from the outlet edge.

Certain of these apparatus are designed so that the user may bear his/her face directly against the outlet edge in use.

Typically, the mask is attached to an operating unit that generates fluid droplets that are entrained in air. The droplets may be generated as by a nebulizer to produce cool mist or may be generated by vaporizing a fluid by using a heat source.

The generated fluid droplets are entrained in an air stream that travels in a path through an outlet for the droplet generator for delivery to the mask volume and ultimate inhalation by a user.

It is common to additionally treat the air stream by using an additive component that is placed in the fluid supply and/or the advancing air stream. These additive components vary widely in terms of their purpose; ranging from simple scents to compositions that may have therapeutic effects. Aromatherapy compositions abound in the industry.

Various different ways have been devised to cause the ultimately delivered air that is inhaled to be treated by the additive composition. In one form, an additive may be placed directly in a fluid, as in a reservoir therefor, before fluid droplets are generated. This approach has a number of drawbacks.

First of all, a liquid additive must be relatively evenly dispersed in the fluid supply to produce a consistent form and quality of inhalable air. In the absence of ongoing mixing, this may not occur.

Further, liquid additives may tend to accumulate on parts of the apparatus, as when they are not thoroughly dissolved, or progressively over time. This may necessitate regular cleaning, which often is not undertaken. Eventually, a buildup of residue from the additive may interfere with operation, such as by inhibiting operation of a nebulizer, etc.

In an alternative form, additive "pads" may be placed in the reservoir. Generally, such pads will not cause an even distribution of additive in the reservoir, whereby the nature and quality of the inhalable air is inconsistent. Spent pads must also be removed through a step that may be difficult to carry out, depending upon the particular design. Generally, portable units may have tight, and difficult to access, spaces in which the pads reside.

In a further form, component "pads" are placed on the operating unit so as to reside within the path of the air stream generated by the operating unit.

First of all, to accommodate one or more absorbent pads commonly used in this manner, space must be provided on the operating unit. This creates the challenge of accommodating the pads while not increasing the overall size of the operating unit. This is particularly a challenge with portable apparatus which are generally compact enough to be grasped in a user's hand.

Commonly, the location reserved for the pad(s) is spaced from the reservoir and situated in such a manner that a special access must be provided to the space/receptacle for the pad(s). It is known to use hinged doors for this purpose. As a result, additional parts are required. Further, small hinged access doors require additional manufacturing steps and the handling of small parts, which is inherently difficult. Still further, small parts are prone to breaking or breaking loose in use, which may compromise the function and/or appearance of the apparatus.

Still further, a dedicated location for one or more pads may lead to the progressive buildup of residue from the pads which ideally would be periodically removed. Aside from the inconvenience of having to do regular maintenance, the small volume provided for the pads may make cleaning an additional challenge which may result in users forgoing this process. The residue itself, or the fluid retained by the residue, may generate bacteria and the like, which is clearly detrimental.

The industry continues to seek out apparatus designs which can afford the option of using additive components without significantly altering the basic apparatus. Further, designers target designs that are user friendly and operate consistently through the anticipated life of an apparatus. Ideally, users have the ability to conveniently clean the overall apparatus, including parts exposed to the additive components, to avoid buildup of bacteria and the like that the user may become exposed to.

SUMMARY OF THE INVENTION

In one form, the invention is directed to a portable air treatment apparatus comprising: a) an operating unit for producing treated air; b) a mask; and c) at least one additive component. The operating unit includes: a reservoir for a supply of fluid; and a fluid treatment unit for generating droplets from a fluid in the reservoir. The operating unit causes generated fluid droplets to be entrained in air and directed in a stream to an outlet for the operating unit. The mask has a body extending around a volume and a surface/edge at an outlet for the volume to be situated near or against a user's frontal face region with the user's face operatively positioned with respect to the mask. The mask body further has an inlet in communication with the volume. The mask and operating unit are configured so that the mask can be releasably operatively connected to the operating unit, whereby the stream of air with entrained fluid droplets flows through the mask body inlet and into the mask body volume. With the user's face operatively positioned with respect to the mask, at least one of the mouth and nose of the user is situated to inhale the stream of air with entrained fluid droplets in and flowing from the mask body volume. The at least one additive component and mask are configured so that the at least one additive component can be placed in an operative position with respect to the mask, wherein the at least one additive component is exposed to the stream of air with entrained fluid droplets flowing into the mask body volume. The mask and at least one additive component in the operative position are movable as a unit relative to the operating unit as the mask is separated from the operating unit.

In one form, the mask body has at least one receptacle configured to receive the at least one additive component with the at least one additive component in the operative position.

In one form, the at least one receptacle is configured to maintain the at least one additive component in the operative position in a predetermined relationship with the mask body.

In one form, the mask body has a wall at which at least a portion of the mask body inlet is located. The at least one receptacle is spaced from the at least portion of the mask body inlet so that the stream of air with entrained fluid droplets moves through the at least portion of the mask body inlet up to, against, and past the at least one additive component, to the volume outlet.

In one form, the at least one receptacle consists of first and second receptacles. The at least one additive component consists of first and second additive components placed respectively in operative positions in the first and second receptacles.

In one form, the at least one additive component is in the form of a discrete pad.

In one form, the at least one receptacle has spaced seats for the at least one additive component.

In one form, the mask body inlet has at least one opening beneath the at least one additive component with the at least one additive component in the operative position.

In one form, the at least one opening consists of a plurality of discrete openings beneath the at least one additive component with the at least one additive component in the operative position. The plurality of discrete openings are located so that the stream of air with entrained fluid droplets moves through each of the plurality of discrete openings up to, against, and past the at least one additive component to the volume outlet.

In one form, the at least one additive component consists of a plurality of additive components each with a flat shape residing in a plane. With the plurality of additive components each in its operative position, the planes of the plurality of additive components are substantially parallel.

In one form, the mask body volume is bounded by a bottom wall. The mask body inlet consists of a plurality of discrete openings in the bottom wall.

In one form, the mask body has at least one receptacle configured to receive the at least one additive component with the at least one additive component in the operative position. The at least one receptacle has spaced seats for the at least one additive component. One of the discrete openings in the bottom wall is located between the spaced seats.

In one form, the at least one receptacle and at least one additive component are configured so that the at least one additive component can be press fit into the at least one receptacle to be releasably maintained in the operative position.

In one form, the at least one receptacle is located so that the at least one additive component can be directed from a fully separated starting position through the volume outlet and into the operative position.

In one form, the at least one receptacle and at least one additive component are configured so that the at least one additive component can be press fit into the at least one receptacle and frictionally maintained in the operative position.

In one form, the at least one additive component has an absorbent body that retains a quantity of a composition that treats the stream of air with entrained fluid droplets as the at least one additive component is exposed to the stream of air with entrained fluid droplets.

In one form, there are connectors on the mask body and operating unit that cooperate to releasably connect the mask body to the operating unit.

In one form, the cooperating connectors are configured so that the mask body and operating unit can be relatively moved from a fully separated relationship towards and against each other into a connected relationship and maintained in the connected relationship without requiring use of separate fasteners.

In one form, the fluid treatment unit is configured to generate the fluid droplets through one of ultrasonic vibration and heating.

In one form, the mask body is molded from a pliable material.

DETAILED DESCRIPTION OF THE PREFERRED EMBODIMENT

Figure 1:
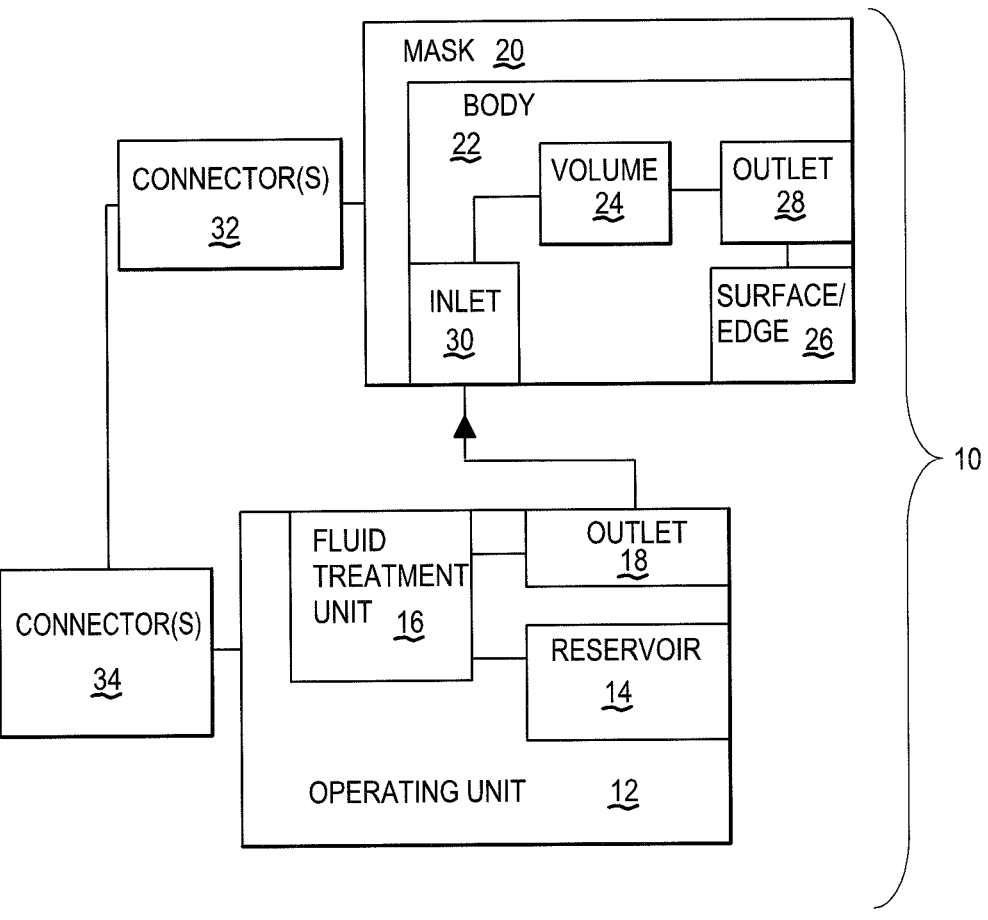
FIG. 1 is a schematic representation of a portable air treatment apparatus, according to the invention.

A portable air treatment apparatus, according to the present invention, is shown schematically at 10 in FIG. 1. The air treatment apparatus 10 consists of an operating unit 12 for producing a treated air supply. The operating unit 12 consists of a reservoir 14 for a supply of fluid and a fluid treatment unit 16 for generating droplets from a fluid in the reservoir 14. The operating unit 12 causes generated fluid droplets to be entrained in air and directed in a stream to an outlet 18 for the operating unit 12.

The air treatment apparatus 10 further includes a mask 20 having a body 22 extending around a volume 24, the body 22 defining a peripheral wall extending around the volume, and a surface/edge 26 on the peripheral wall at an outlet 28 for the volume 24. The surface/edge 26 is configured to be situated near or against a user's frontal face region with the user's face operatively positioned with respect to the mask 20.

The mask body 22 further has an inlet 30 in communication with the volume 24.

The mask 20 and operating unit 12 are configured so that the mask can be releasably operatively connected to the operating unit through at least one connector 32 on the mask that cooperates with at least one connector 34 on the operating unit 12. The connectors 32, 34 may be engageable with or without the requirement of fasteners, separate from the mask 20 and/or operating unit 12.

With the mask operatively connected to the operating unit, a stream of air with entrained fluid droplets flows from the outlet 18 on the operating unit 12 through the mask body inlet 30 and into the mask body volume 24. With a user's face operatively positioned with respect to the mask 20, at least one of the mouth and nose of the user is situated to inhale the stream of air with entrained fluid droplets in, and flowing from, the mask body volume 24.

Figure 2:
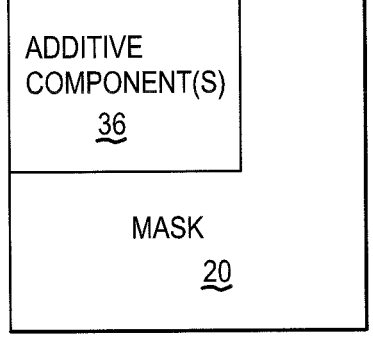
FIG. 2 is a schematic representation of additional details of a mask as shown on the portable air treatment apparatus in FIG. 1 and including at least one additive component.

As shown schematically in FIG. 2, at least one additive component 36 is provided. The at least one additive component 36 and mask 20 are configured so that the at least one additive component 36 can be placed in an operative position with respect to the mask, wherein the at least one additive component 36 is exposed to the stream of air with entrained fluid droplets flowing into the mask body volume 24.

With the at least one additive component 36 in the operative position, the mask 20 and at least additive component 36 are movable as a unit relative to the operating unit 12 as the mask 20 is selectively joined to and separated from the operating unit 12.

Figure 3:
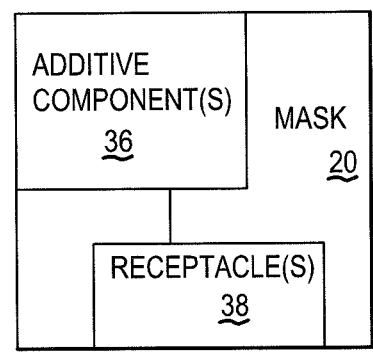
FIG. 3 is a schematic representation of one form of a mask as shown in FIG. 2 and including a receptacle for the at least one additive component.
Figure 4:
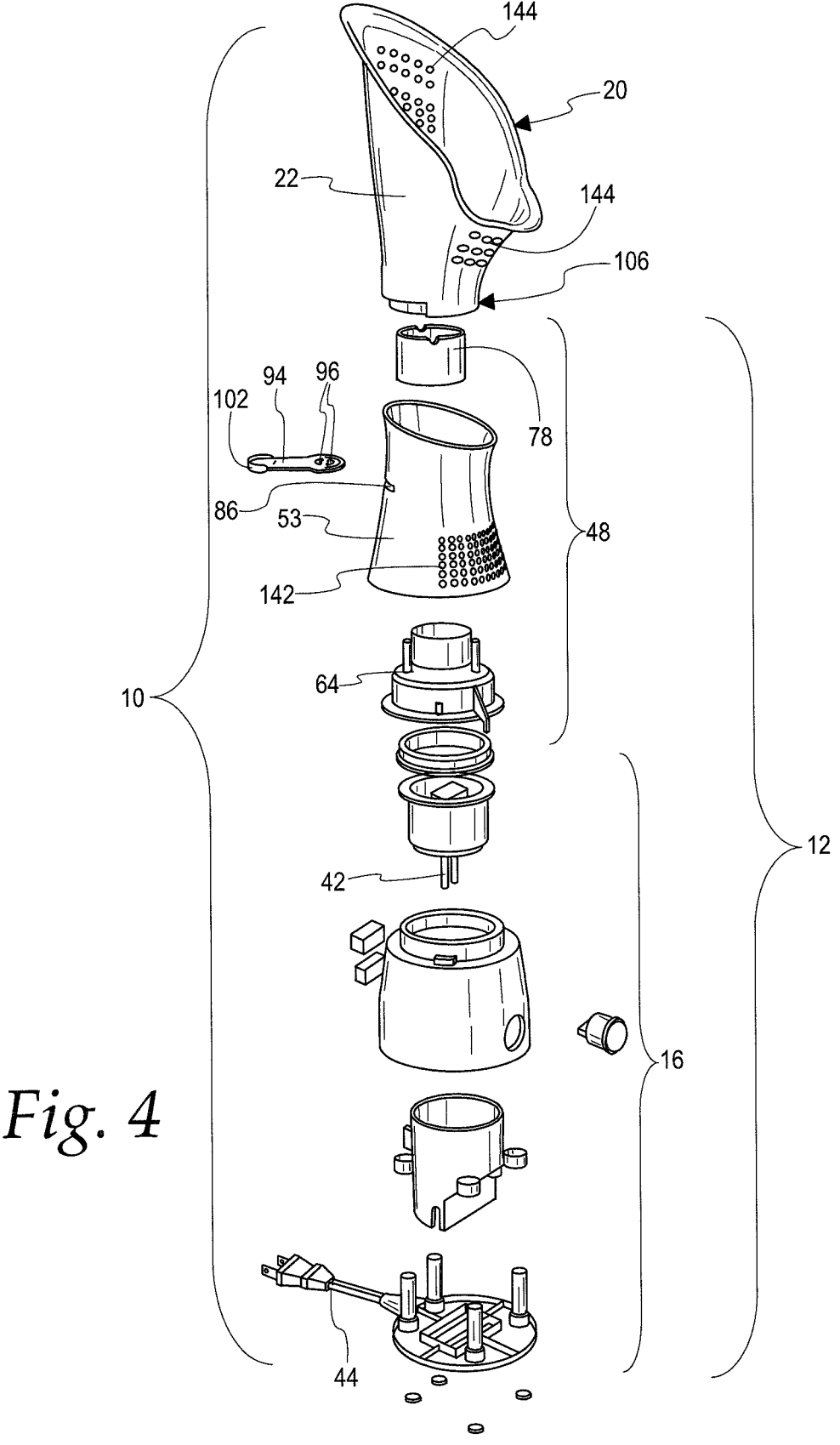
FIG. 4 is an exploded perspective view of one exemplary form of the inventive portable air treatment apparatus, as shown schematically in FIGS. 1-3.
Figures 5, 6:
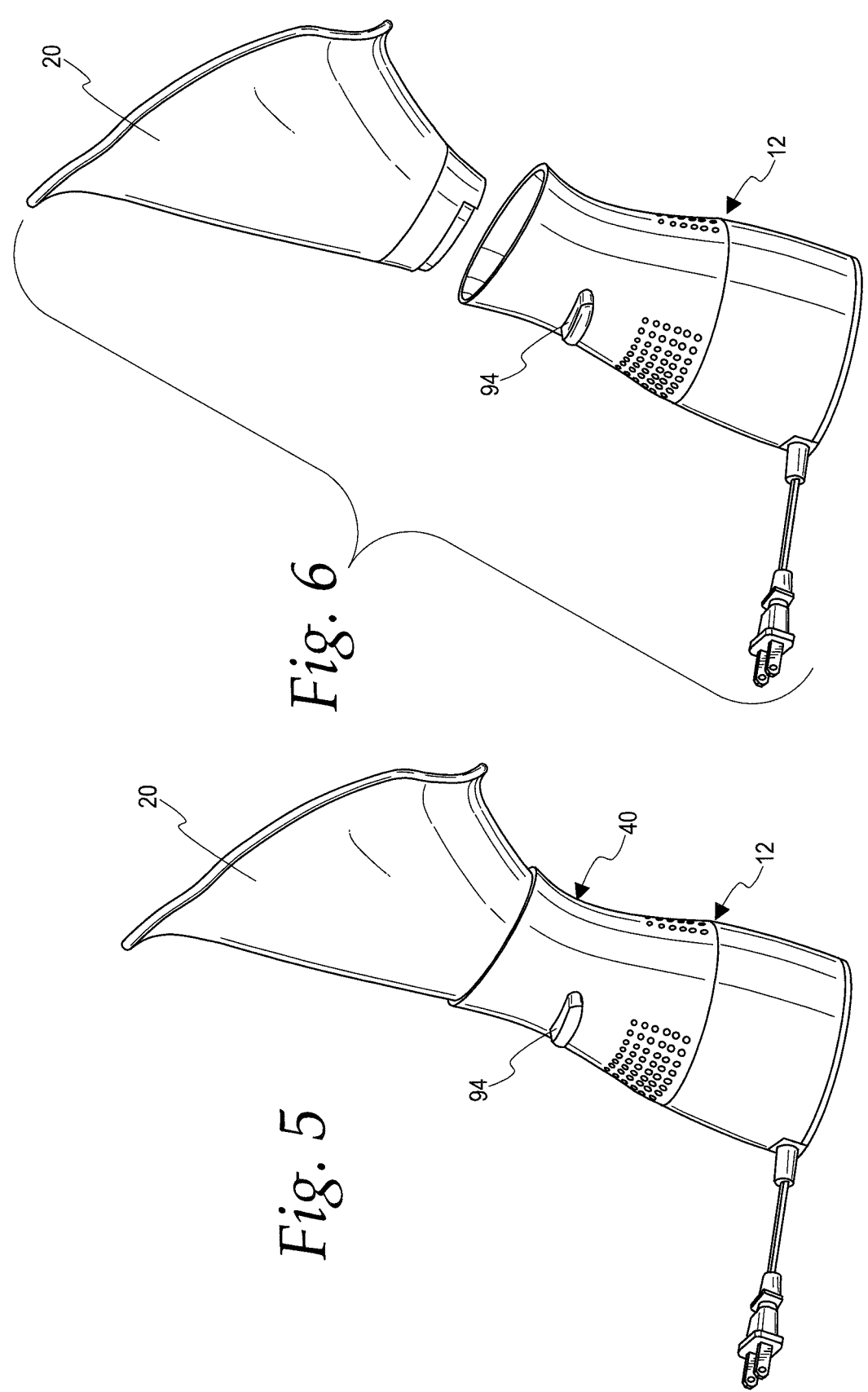
FIG. 5 is a side elevation of the portable air treatment apparatus in FIG. 4 with the components in an assembled state.
FIG. 6 is a partially exploded view of the portable air treatment apparatus as in FIG. 4 wherein a mask is separated from an operating unit.
Figures 7, 8:
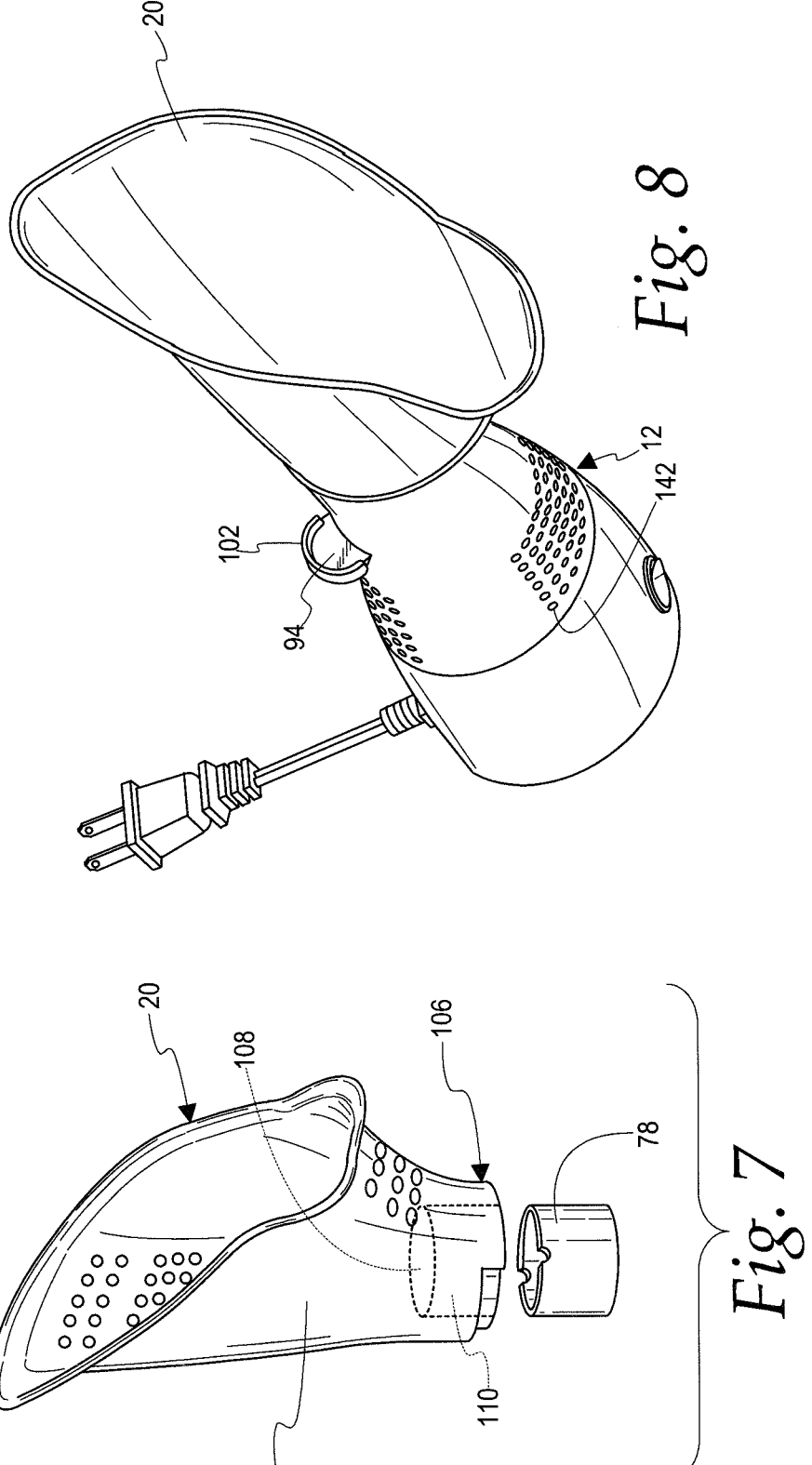
FIG. 7 is an exploded perspective view of the mask as shown on the portable air treatment apparatus in FIGS. 4-6 and in relationship to a mounting base on the operating unit.
FIG. 8 is a view of the components as in FIG. 5 and from a different perspective.
Figures 9, 10:
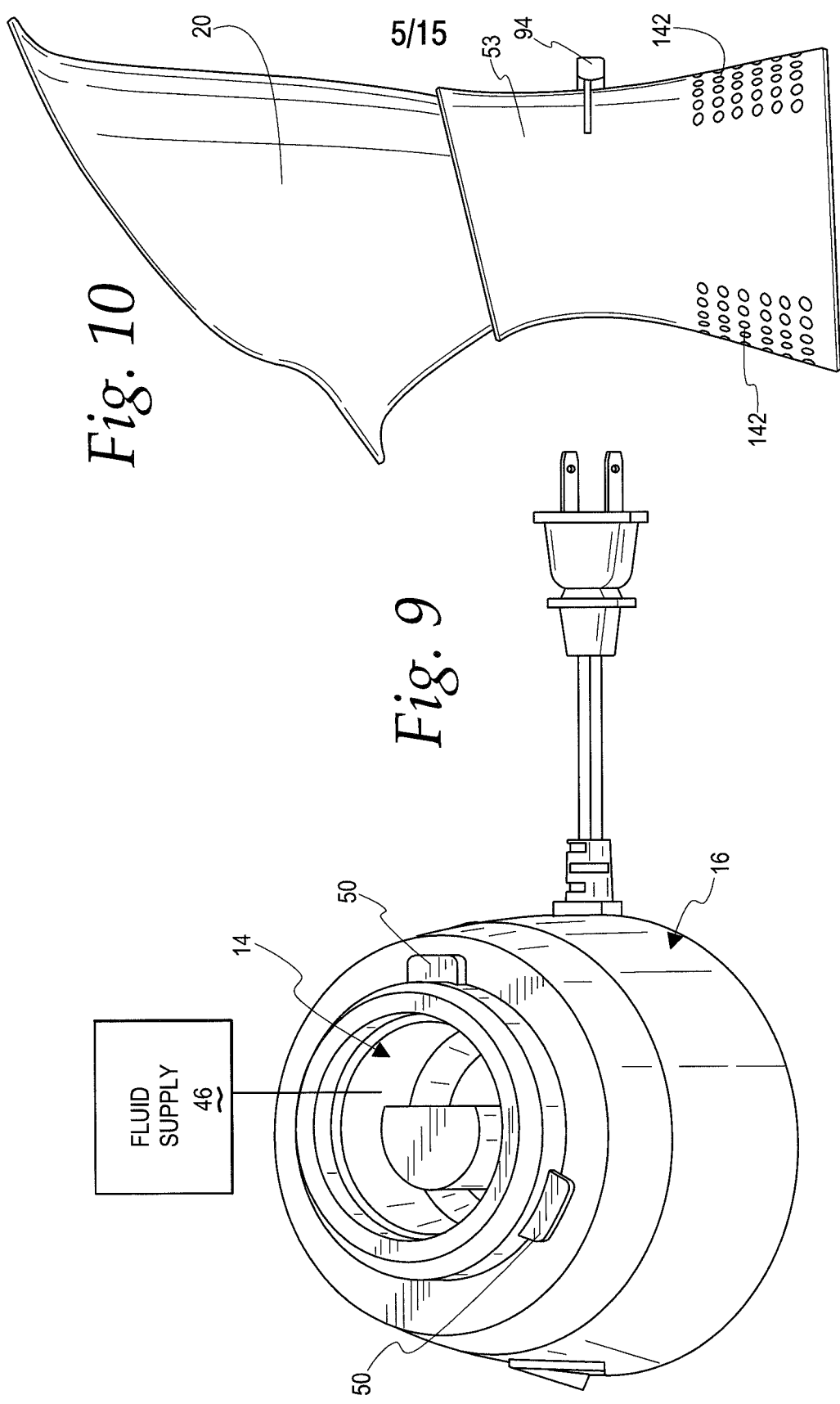
FIG. 9 is a perspective view of a fluid treatment unit on the portable air treatment apparatus shown in FIGS. 4-8.
FIG. 10 is a side elevation view of the mask and a housing on the operating unit, making up part of the portable air treatment apparatus in FIGS. 4-9.
Figure 12:
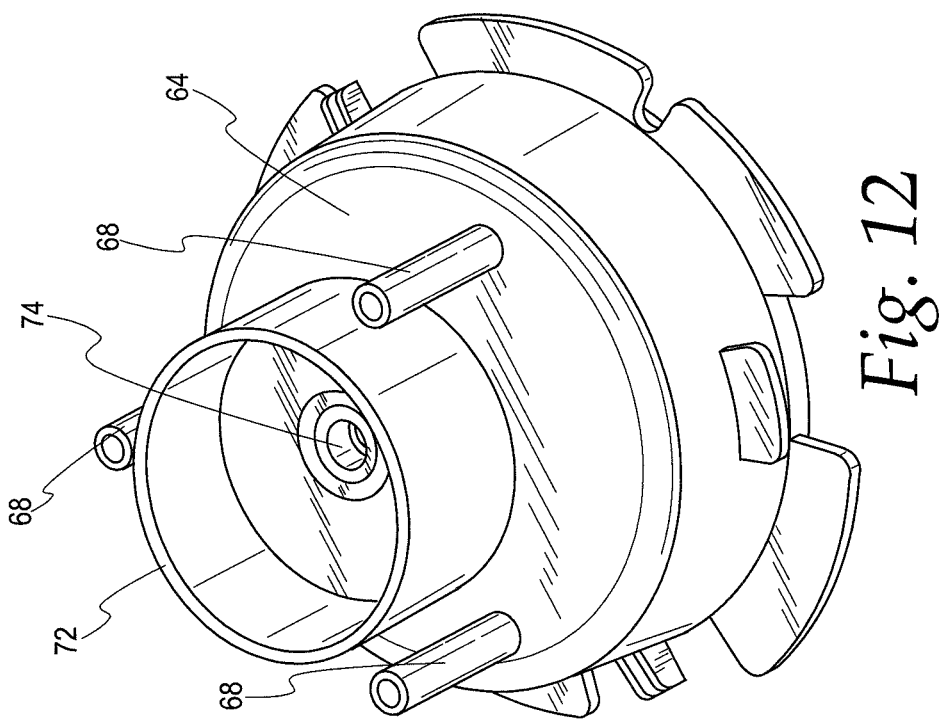
FIG. 12 is a bottom perspective view of a flow adaptor making up part of the inventive operating unit.
Figure 11:
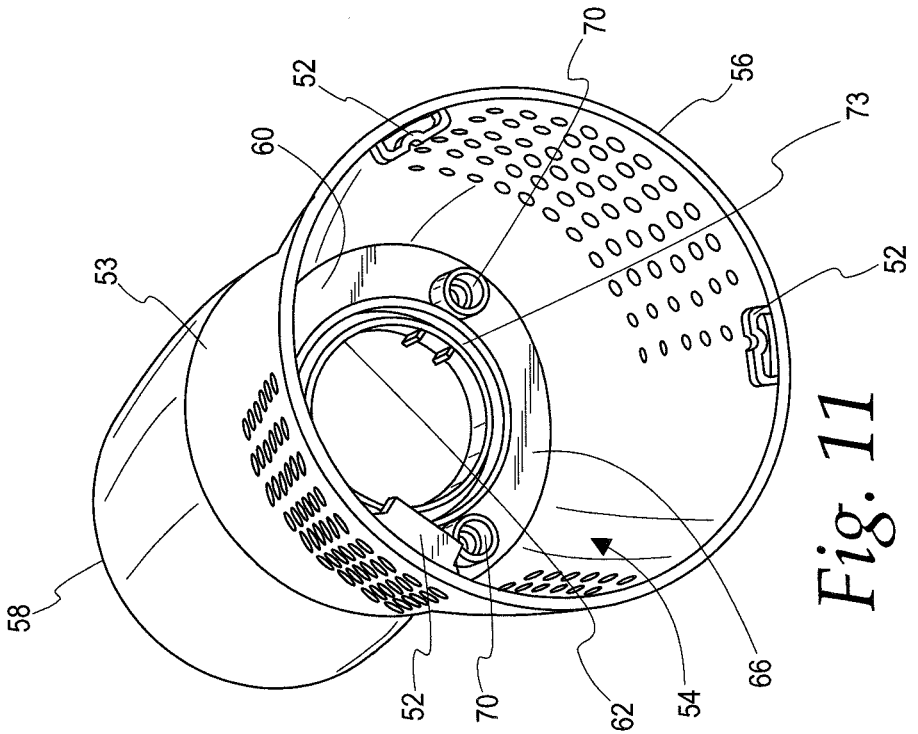
FIG. 11 is a bottom perspective view of the housing as shown in FIG. 10.
Figures 13, 14:
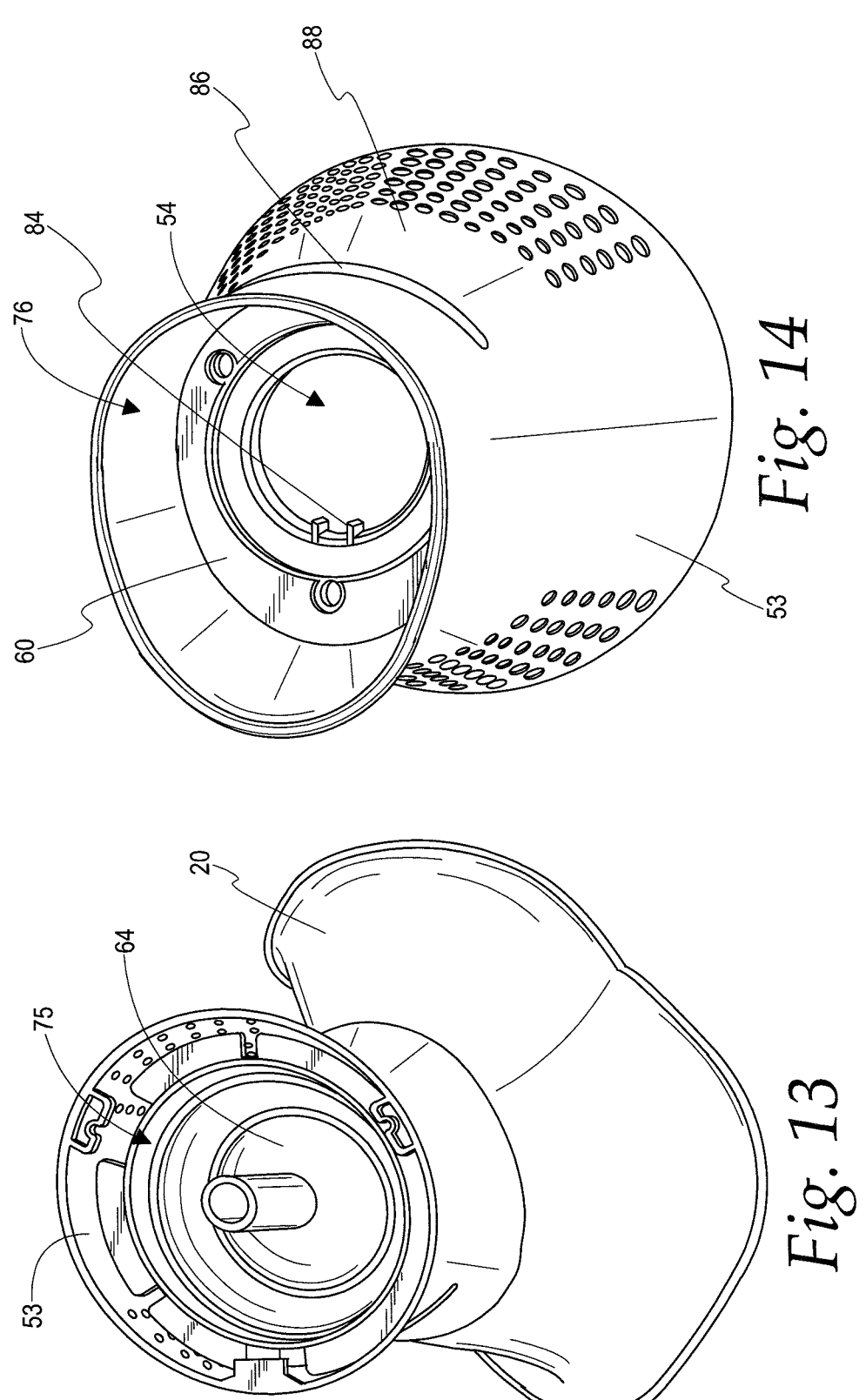
FIG. 13 is a bottom perspective view showing the flow adaptor in FIG. 12 connected to the housing as shown in FIGS. 10 and 11.
FIG. 14 is a top perspective view of the housing as shown in FIG. 11.
Figure 16:
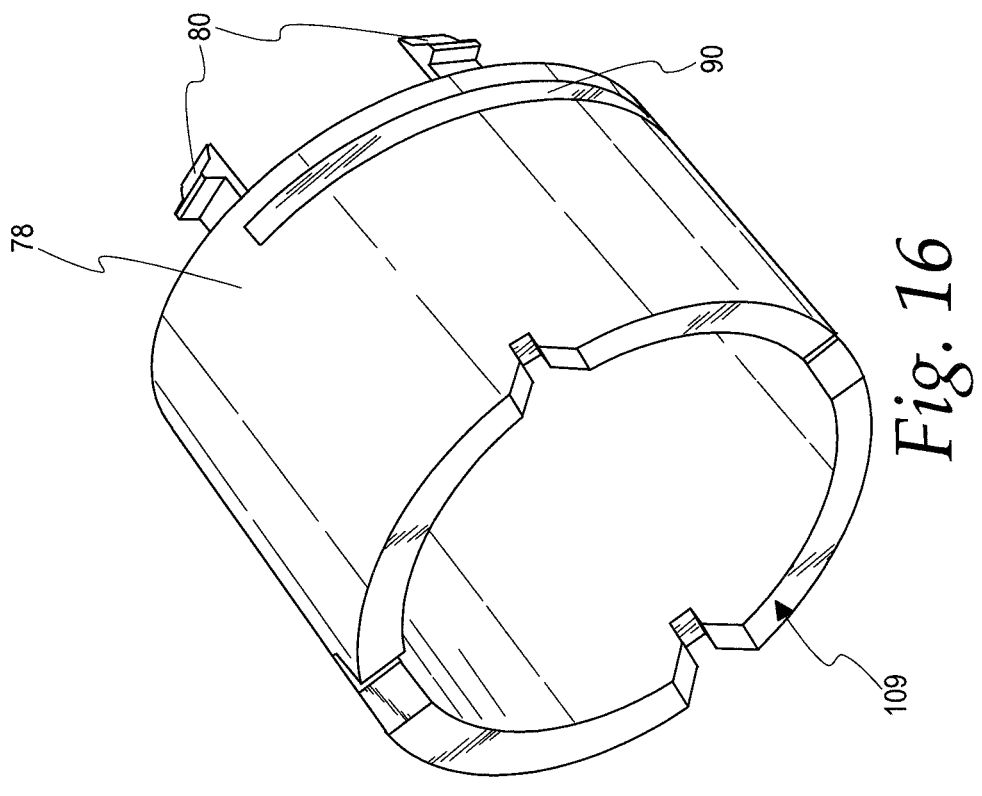
FIG. 16 is a view of the mounting base in FIG. 15 from a different perspective.
Figure 15:
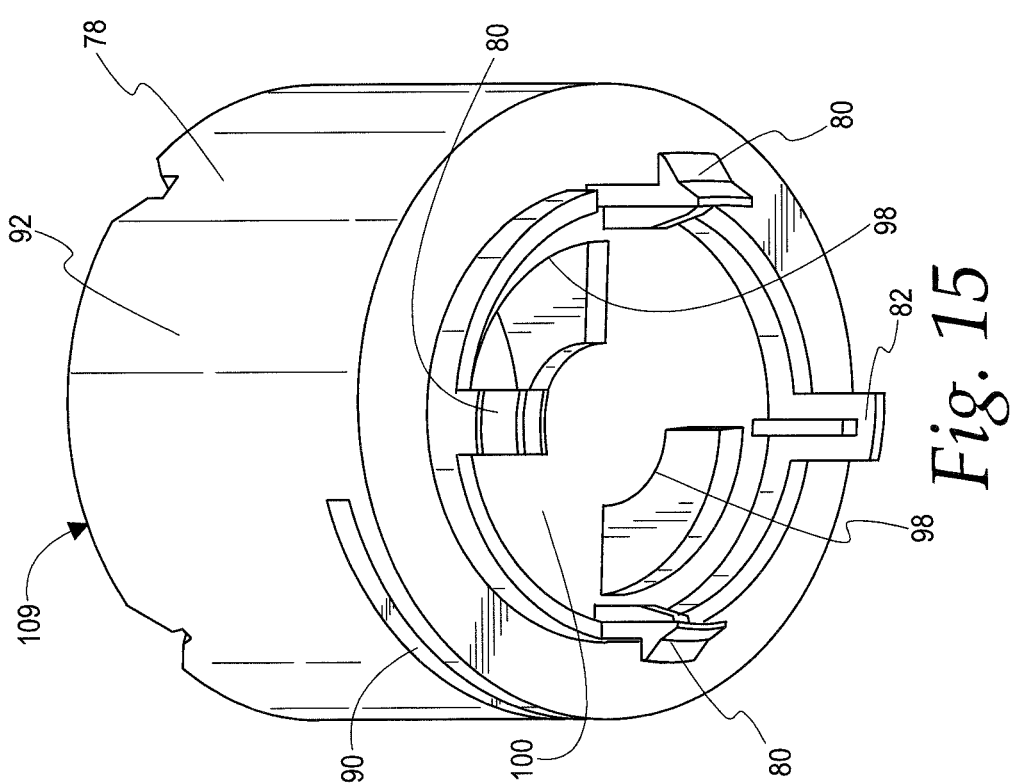
FIG. 15 is a bottom perspective view of a mounting base making up part of the operating unit on the inventive portable air treatment apparatus.
Figures 17, 18:
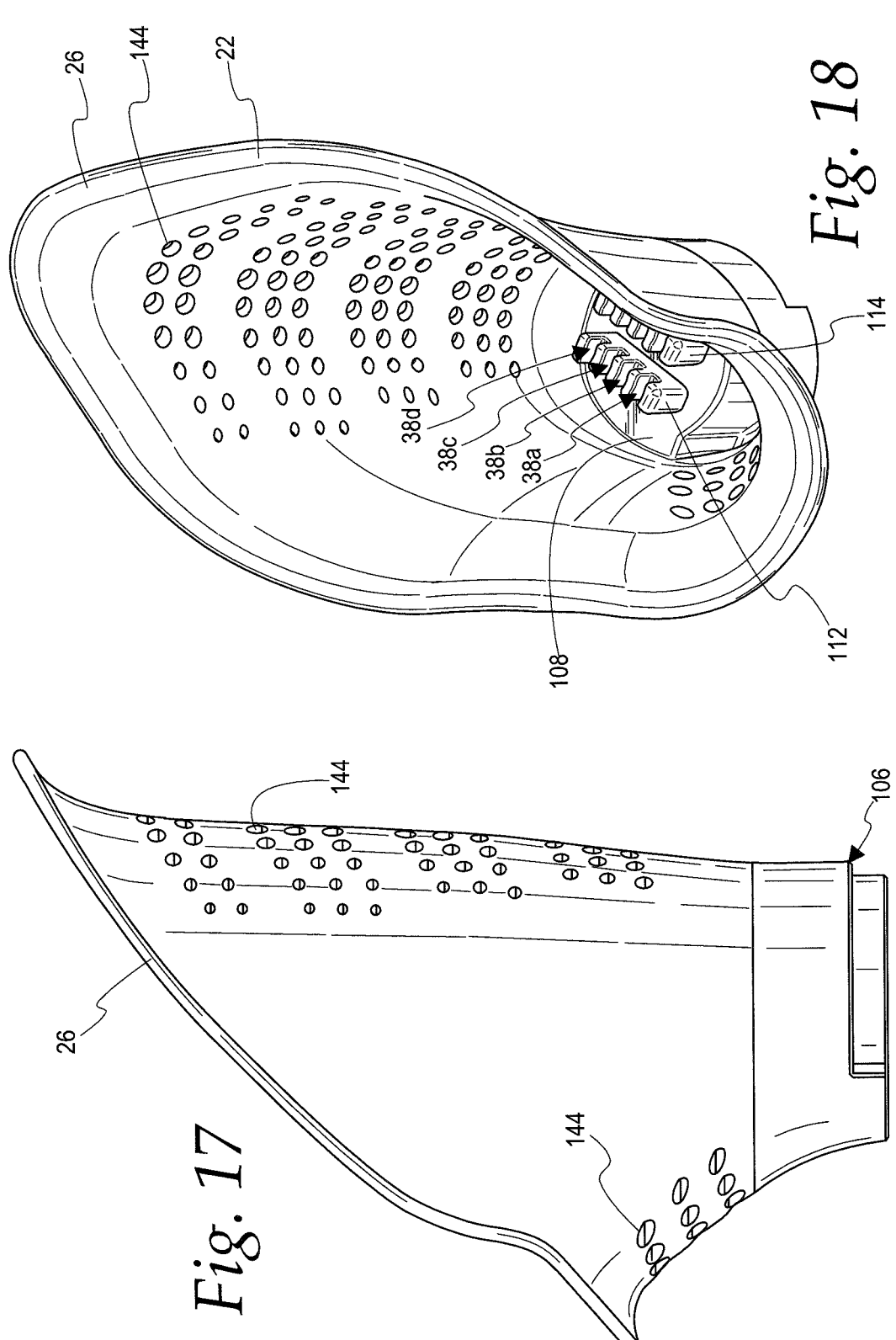
FIG. 17 is a side elevation of the mask on the inventive portable air treatment apparatus.
FIG. 18 is a top perspective view of the mask in FIG. 17.
Figures 19, 20:
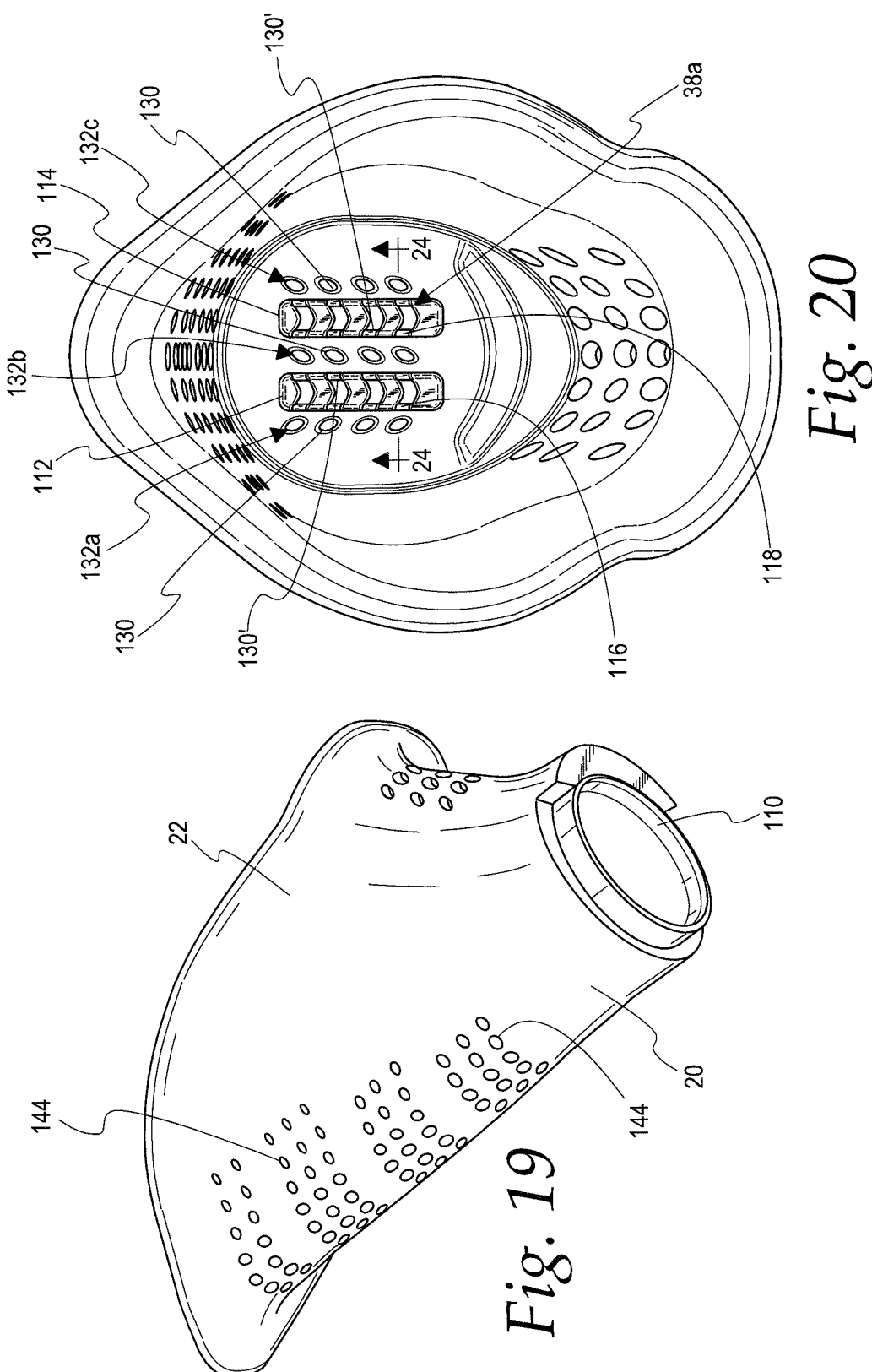
FIG. 19 is a bottom perspective view of the mask in FIGS. 17 and 18.
FIG. 20 is a top view of the mask in FIGS. 17-19.
Figures 21, 22:
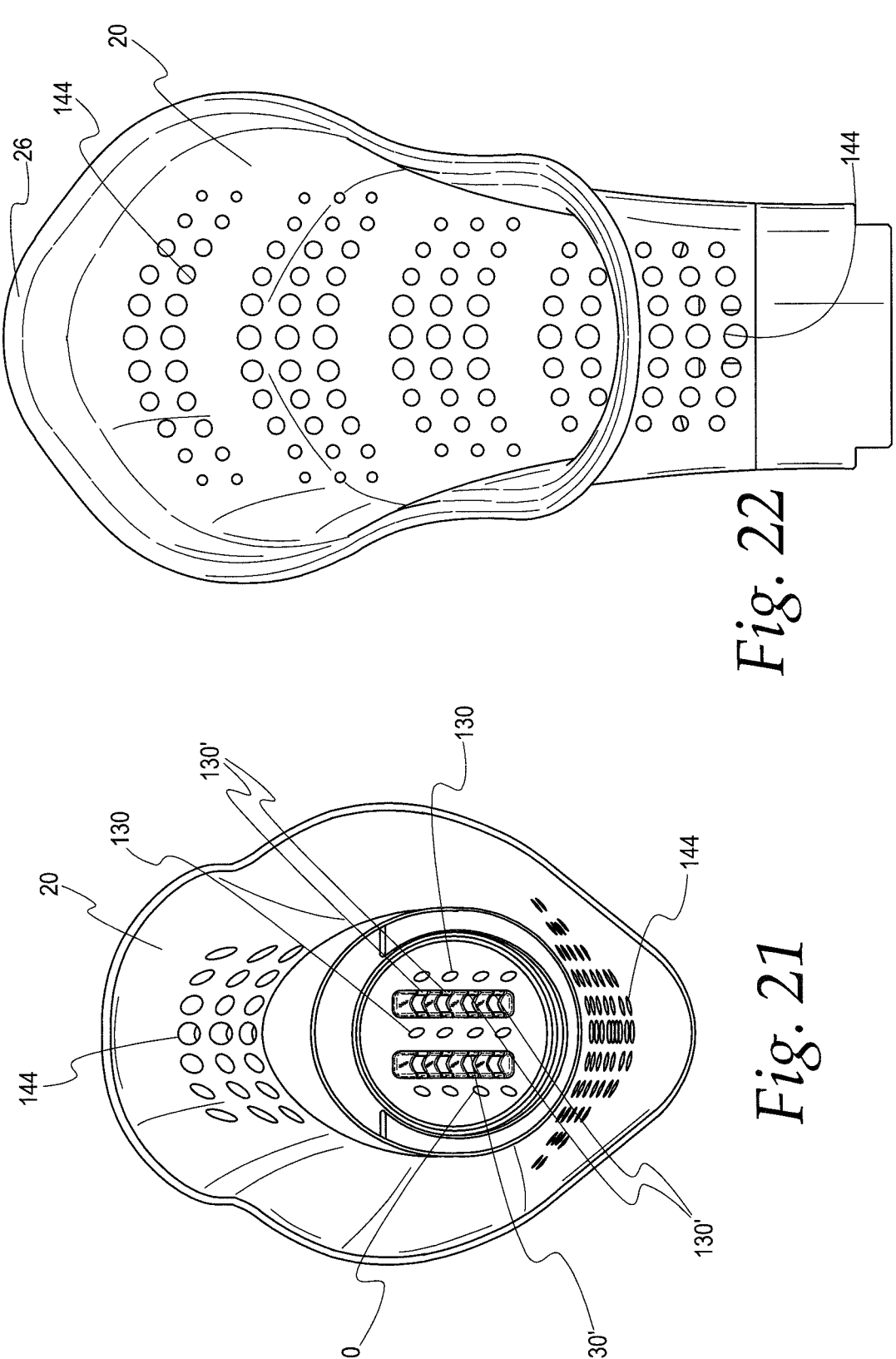
FIG. 21 is a bottom view of the mask in FIGS. 17-20.
FIG. 22 is a front elevation view of the mask in FIGS. 17-21.

In one exemplary form, as shown schematically in FIG. 3, the mask 20 may have least one receptacle 38, each configured to receive at least one additive component 36 with the additive component 36 in the operative position.

In FIGS. 1-3, all components and are depicted schematically to encompass virtually an unlimited number of different variations of each of the individual components and their interactions.

One focus herein is upon the incorporation of the at least one additive component 36 into the mask 20, into an operative position thereon, to be movable therewith as a unit which can be releasably connected to, and separated from, the operating unit 12. The details of the operating unit 12 are not critical to the present invention, with it being understood that a multitude of different structures may be utilized to generate fluid droplets that are either cool or heated. The fluid treatment unit 16 may include a nebulizer, a heating element, etc. to generate the fluid droplets. The present invention is not limited to any specific form of the operating unit, any type of fluid from which the droplets are formed, or the droplets themselves, so long as the droplets can be entrained in air and directed in a controlled stream from the outlet 18 on the operating unit 12 into the mask volume 24.

Further, while an exemplary form of the apparatus will be described below, the at least one additive component 36 may be placed in an operative position in different ways including, but not limited to, by providing a discrete receptacle 38 that is designed specifically for the at least one additive component 36.

Referring now to FIGS. 4-25, one exemplary form of the portable air treatment apparatus 10 will be described.

The depicted apparatus 10 has an operating unit 12 to which the mask 20 is releasably connected. The operating unit 12 has a generally cylindrical external shape with a locally reduced diameter region at 40 that facilitates comfortable and positive grasping thereof, as in the hand of a user.

The fluid treatment unit 16 on the operating unit 12 incorporates a heater 42 that may be self-powered, as by a battery (not shown). As depicted, the heater 42 is connectable to a household power supply through a corded, male plug 44.

The heater 42 elevates the temperature of fluid in a supply 46 thereof within the reservoir 14 to produce droplets which may be, but are not limited to, water droplets.

Between the mask 20 and fluid treatment unit 16, a flow control section 48 is provided. In the depicted form, the flow control section 48 is releasably joined to the fluid treatment unit 16 through a bayonet-type connection with cooperating connector parts 50 on the fluid treatment unit 16 and connector parts 52 on the flow control section 48.

The flow control section 48 has a housing 53 bounding a through passage 54 between a bottom 56 and top 58 thereof. A wall 60 is provided between the top 58 and bottom 56 of the housing 53 and defines a locally reduced diameter opening 62.

A flow adaptor 64 is fit against the underside 66 of the wall 60 with locating posts 68 thereon pressed, one each, into receptacles 70 at the underside 66 of the wall 60. The flow adaptor 64 has an inverted funnel shape with an annular upper edge 72 that seats in a complementarily-shaped, downwardly opening annular seat 73 on the wall 60. The flow adaptor 64 defines a reduced diameter through opening 74 which communicates from a volume, 75 bounded by the flow adaptor 64 and housing 53, to a volume 76 within the passage 54 above the wall 60.

A mask mounting base 78 is snap fit to the top of the wall 60 using three bendable legs 80 that are progressively deformed through a camming action as the mounting base 78 is lowered to against the wall 60, whereupon they spring back to capture the wall 60. A locating tab 82 on the mounting base 78 is alignable with an opening 84 on the wall 60 to facilitate placement of the mounting base 78 in a consistent angular orientation wherein an arcuate slot 86, through a peripheral wall 88 on the housing 53, aligns with and is coextensive with a slot 90 through a peripheral wall 92 on the mounting base 78 that extends around the volume 76.

A control gate 94 is slidable guidingly through the aligned slots 86, 90 radially inwardly and outwardly to control a relationship between openings 96 on the gate 94 and openings 98 through a wall 100 of the mounting base 78.

A graspable, externally situated rim 102 is engageable by a user and facilitates radial movement of the gate 94 in opposite directions. This movement changes the degree of registration of the openings 96, 98 to thereby control the flow rate/volume through the wall 100 and into the volume 76.

In this embodiment, a lower region at 106 of the mask body 22 is press fit into the open top region of the flow control section 48 so that a bottom wall 108 bounding the mask volume 24 resides at or adjacent the top 109 of the mounting base 78. Cooperating surfaces on the mask body 22 and flow control section 48 are non-round, as viewed from above, so that the mask body 22 can be consistently placed and blocked against turning around a vertical axis relative to the flow control section 48.

In this embodiment, the aforementioned connectors 32, 34 may be frictionally engaging surfaces on the mask 20 and housing 53. The bottom wall 108 is elevated above the bottom of the mask body 22 by a sleeve 110, formed integrally with the body 22 of the mask 20 and which surrounds, and frictionally embraces, the wall 92 on the mounting base 78, thereby forming another cooperating connector arrangement. Additional connectors 32, 34, such as press fitting or snap fitting connectors, might be utilized to establish a more tenacious connection and maintain a consistent assembled relationship between the mask 20 and housing 53. As depicted, but not required, the bottom wall 108 bears against the top 109 of the mounting base 78 with the mask 20 connected to the operating unit 12.

In this embodiment, the bottom wall 108 has a plurality of the receptacles 38a, 38b, 38c, 38d formed thereon. As indicated previously, a single receptacle 38 might be provided, or more than the four receptacles 38 depicted might be provided.

As depicted, spaced, elongate, raised, bosses 112, 114 are provided on the wall 108 and cooperatively define the four like receptacles 38a, 38b, 38c, 38d within the peripheral wall bounding the volume 24.

As seen for the exemplary receptacle 38a, the bosses 112, 114 are undercut to define spaced seats 116, 118. The undercuts are configured to allow an exemplary form of the additive component 36 to span the bosses 112, 114 and be press fit into the undercuts to against the seats 116, 118.

Figures 23, 24, 25:
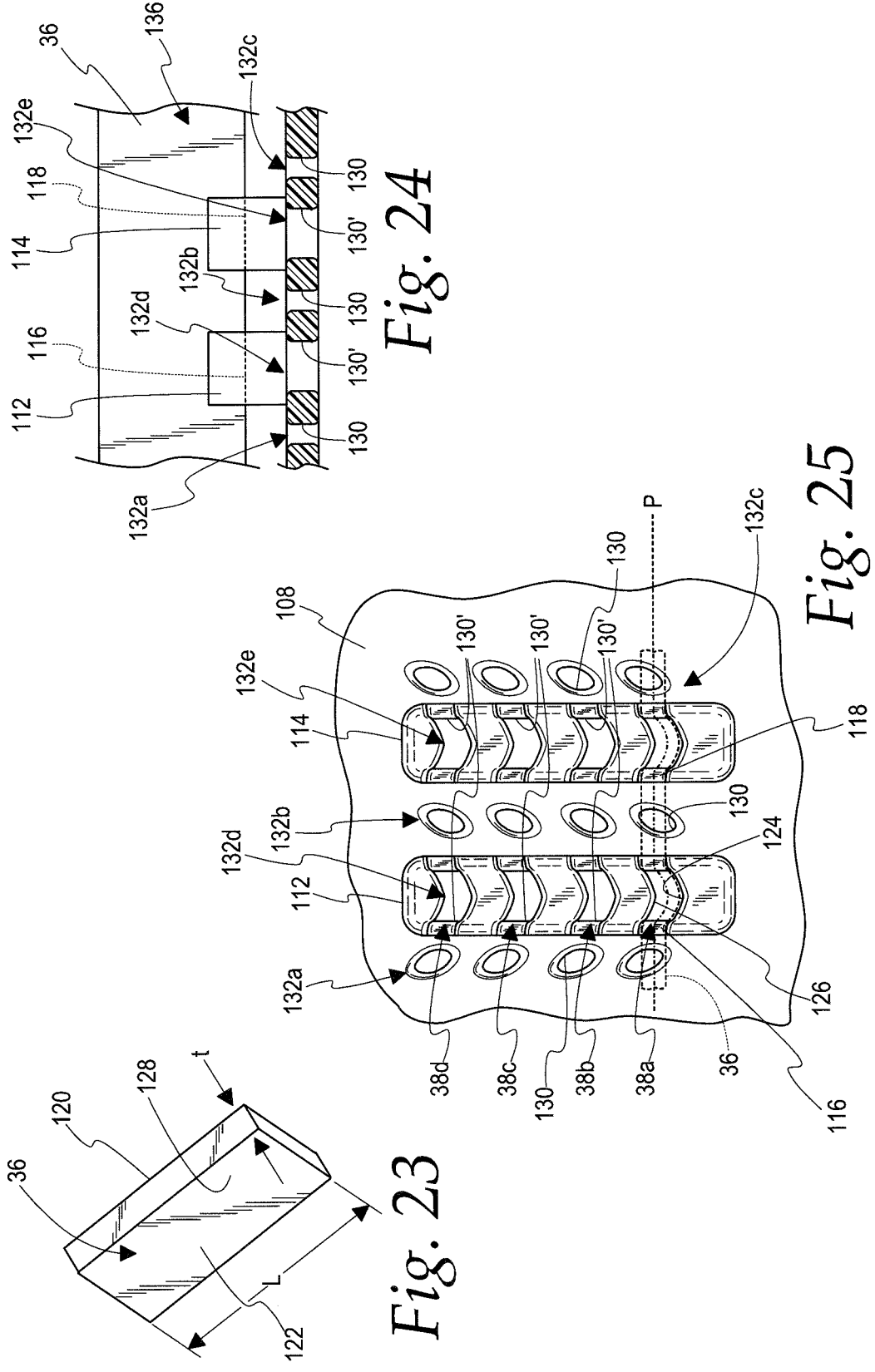
FIG. 23 is a perspective view of one form of additive component, as shown schematically in FIG. 2.
FIG. 24 is a fragmentary, cross-sectional view of a portion of the mask taken along line 24-24 of FIG. 20 and showing the additive component in FIG. 23 in an operative position with respect to the mask.
FIG. 25 is a fragmentary, top view of a portion of the mask in FIGS. 17-22 and showing four different additive components, as in FIG. 23, each in an operative position with respect to the mask.
Figure 27:
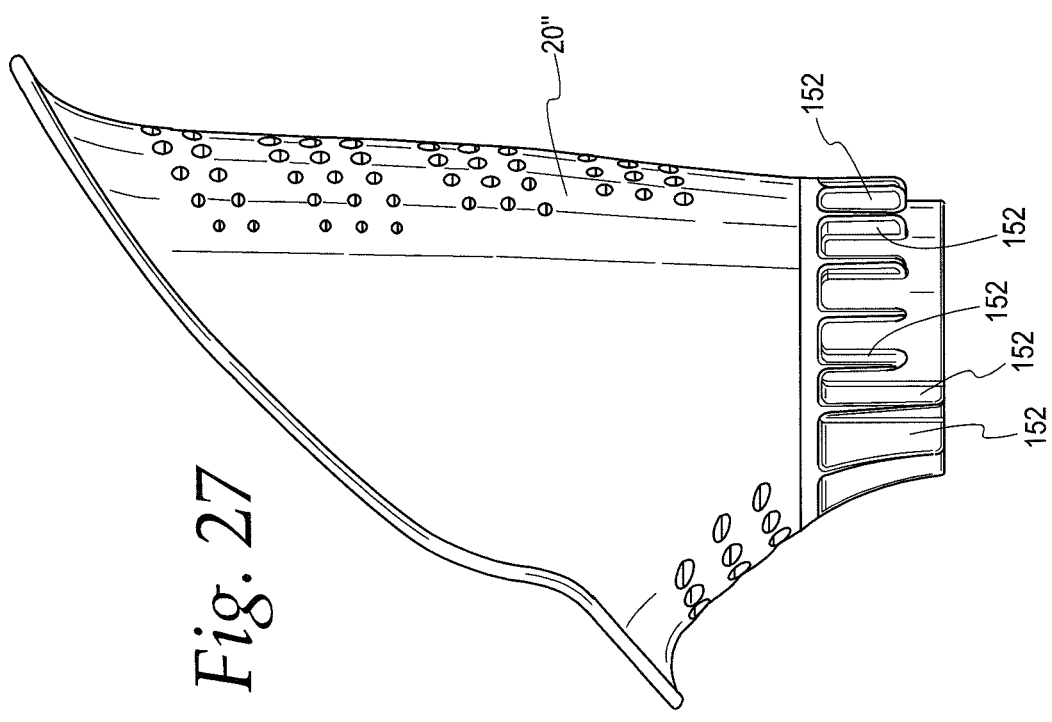
FIG. 27 is a side elevation view of the mask in FIG. 26.
Figure 26:
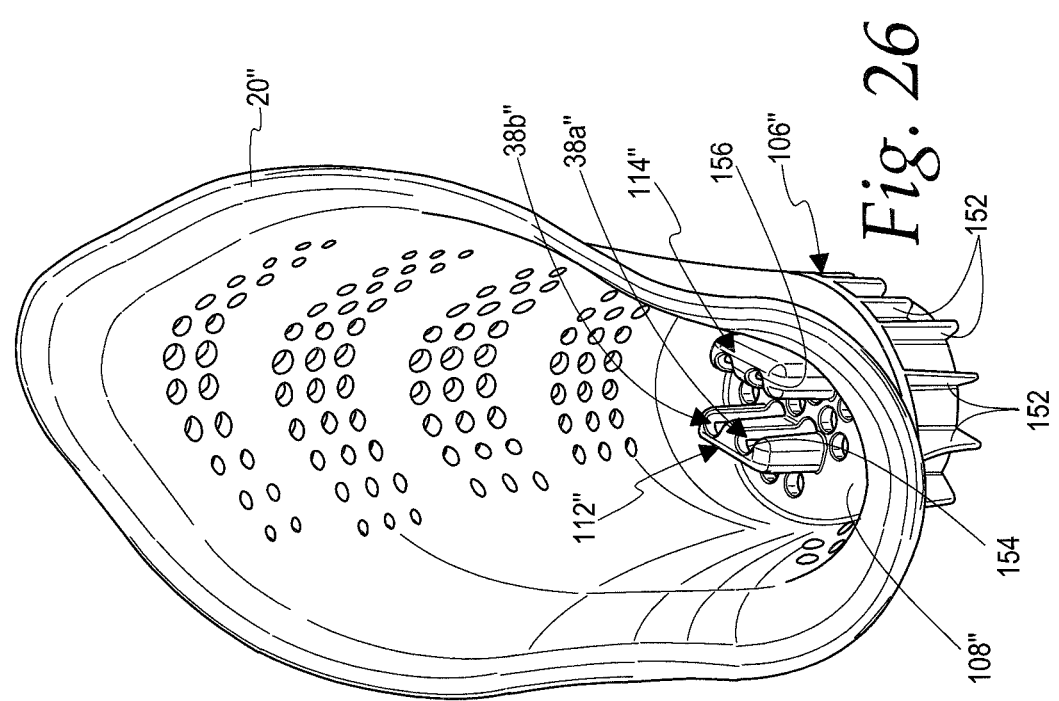
FIG. 26 is a perspective view of a modified form of mask, according to the present invention.
Figures 28, 29:
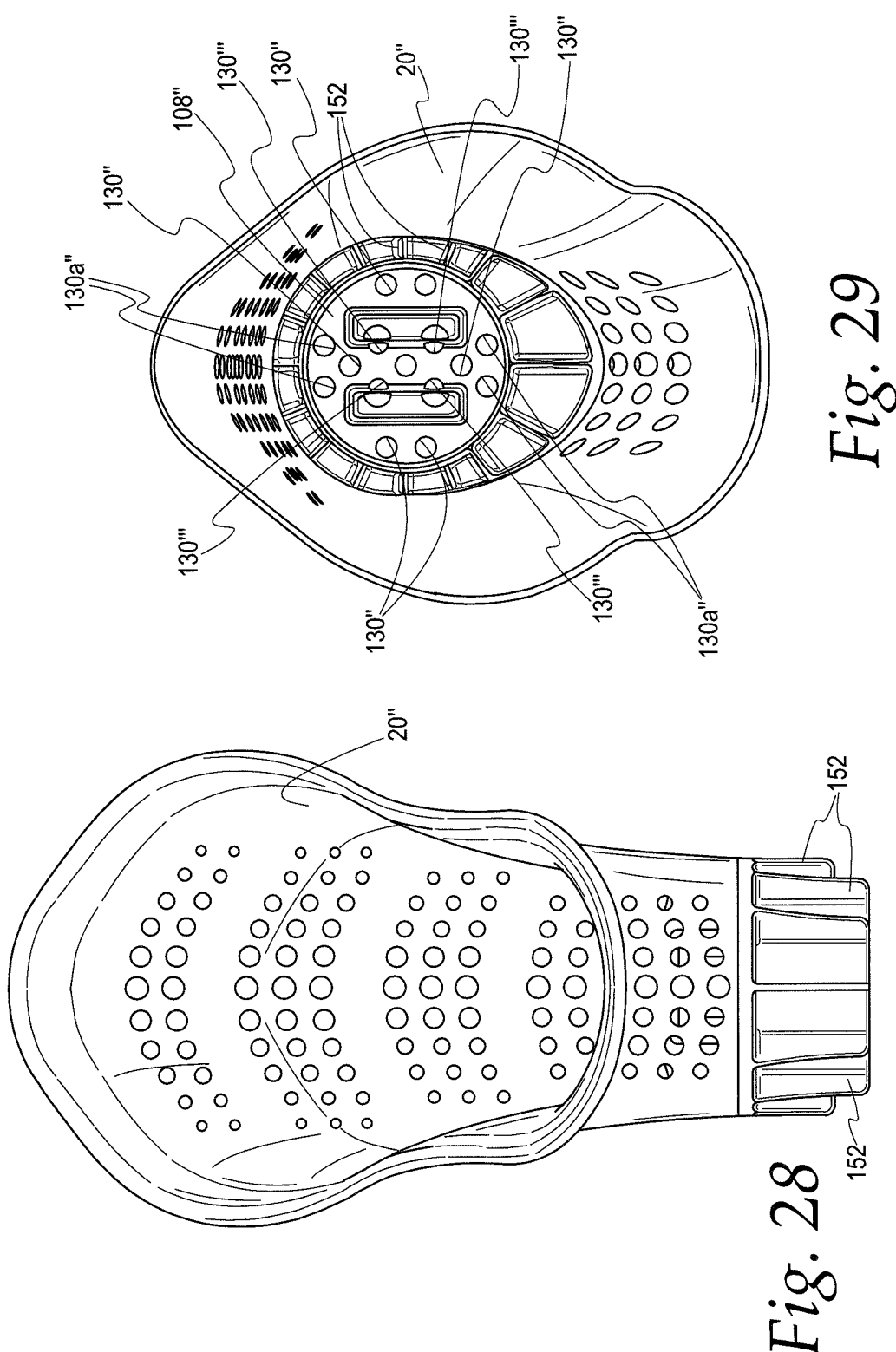
FIG. 28 is a front elevation view of the mask in FIGS. 26 and 27.
FIG. 29 is a bottom view of the mask in FIGS. 26-28.
Figure 30:
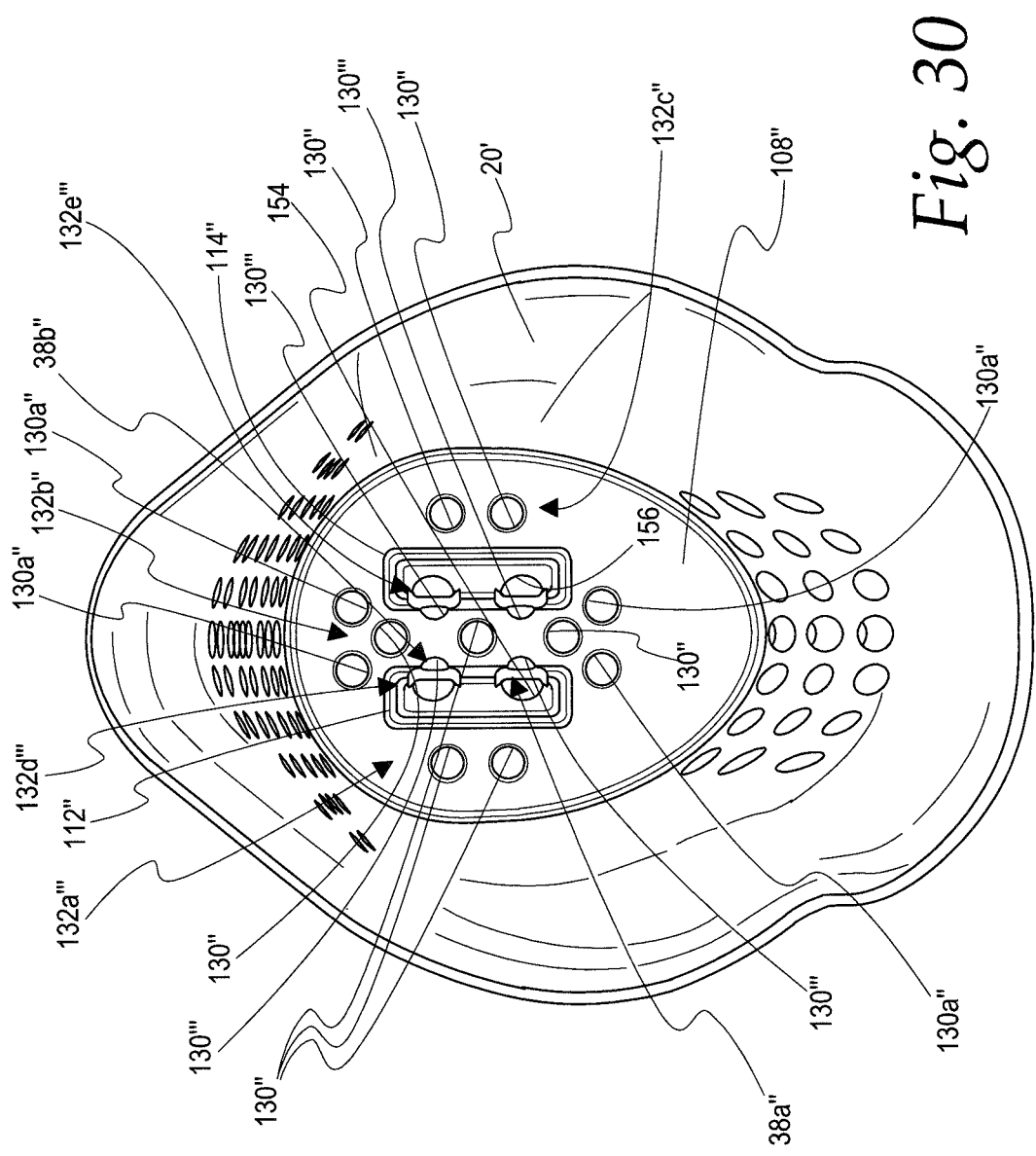
FIG. 30 is a top view of the mask in FIGS. 26-29.

As depicted in FIG. 23, an exemplary additive component 36 has a generally rectangular shape with a thickness t between oppositely facing side surfaces 120, 122. The depicted undercut region on the exemplary boss 112 is bounded by concave and convex surfaces 124, 126 which are spaced so that the thickness t of the body 128 of the additive component 36 is slightly pinched and bent upon being pressed to against the seat 116. A similar arrangement is provided on the boss 114. Accordingly, the additive component 36 can be simply press fit into place and will be slightly deformed and frictionally held in its operative position as depicted in FIGS. 24 and 25. By a simple press fit step, each of the additive components 36 can be directed into its operative position in its respective receptacle 38 to be maintained in a predetermined relationship with the mask body 22.

As seen in FIG. 25, but not required, the planes (P for the exemplary additive component 36 operatively positioned in receptacle 38a) that the flat operatively positioned additive components 36 occupy are substantially parallel and spaced from each other equidistantly.

With this arrangement one, or up to four, of the additive components 36 can each be press fit into its operative position and will be releasably maintained in a predetermined relationship with the mask body 22. The open volume 24 permits easy access to the receptacles 38 through the outlet 28 whereby the additive components 36 can be conveniently pressed thereinto and withdrawn therefrom.

All of the exposed regions of the bosses 112, 114 are rounded so as to guide the additive components 36 thereover without hang-up.

The outlet 18 shown schematically in FIG. 1 is generally through the registered openings 96, 98 through which air flow is delivered to the volume 76.

The inlet 30 on the mask body 22 is formed at least partially through the wall 108 and consists of a plurality of discrete openings 130 of one general size and shape and a plurality of discrete openings 130' having a different size and shape. The precise number and shape of the openings 130 could be changed from that shown. The depicted size and shape of the openings 130, 130' is not required. Further, the openings 130 may have different sizes and shapes. The openings 130' may also have different sizes and shapes.

As shown, the openings 130, 130' are provided in five substantially parallel rows 132a, 132b, 132c, 123d, 132e. The row 132a of openings 130 is at one side of the boss 112 to reside spaced from, and in this form beneath, one end region at 134 of the operatively positioned additive component 36, with the row of openings 130 at 132c having a similar relationship at the other end region 136 of the operatively positioned additive component 36. The row 132b of discrete openings 130 resides between the bosses 112, 114.

The rows 132d, 132e of the openings 130' extend through the bosses 112, 114, respectively, and, as depicted, openings 130' in the rows 132d, 132e are located, one each, directly beneath a part of an additive component 36 in a respective receptacle 38.

With this arrangement, the air with the entrained particles flows in a path upwardly through the openings 130, 130' through the wall 108, to against the additive components 36, and past the additive components 36 to the outlet 28 for the mask 22. The outlet 28 is generally considered to be that region defined at the surface 26 which is the top of the wall 136 that bounds the volume 24. The arrangement of the discrete openings 130, 130' effectively immerses the operatively mounted additive components 36 in the air with the entrained droplets so that there is a substantial surface area contact with the additive components 36. The air stream flow is preferably adequate to continuously flow against and past the operatively positioned additive components 36 while continuously filling the volume 76 during operation.

The discrete openings 130, 130' may define the entirety of the inlet 30 or only a portion thereof.

While not limited, the exemplary form of the additive components 36 is a discrete pad shape that may be absorbent so as to retain and over time progressively release an absorbed composition that moves with the air stream to be inhaled. The composition is not limited in nature and may be aromatic and/or therapeutic, etc.

In the depicted embodiment, the body 22 of the mask has a conventional shape common to masks that are placed against a frontal face region of a user and conformingly cover the nose and mouth. This shape is not required and is only exemplary in nature. Further, it may be desirable that the user not press his/her face directly against the surface 26 but rather that a slight gap be maintained to avoid contact with the surface that might transfer bacteria or other foreign substances.

The mask body 22 may be made from a pliable material, such as silicone, but pliability is not required. This form makes possible one piece molding of the mask, including the sleeve 110.

As explained, the mask 20 may be simply press fit to the operating unit 12 and frictionally held. Alternatively, additional connectors might be utilized as to snap connect or otherwise maintain the assembled relationship of the mask 20 and operating unit 12.

The ability to separate the mask 20 together with the additive components 36 has a number of advantages. Aside from not requiring accommodating structure on the operating unit 12, it is convenient for the user to manipulate the separated mask 20 to access the volume 24 to operatively insert and withdraw the additive components 36.

Further, the mask 20 may be made from a material that is easily washed, as in a dishwasher. Accordingly, the regions of the mask 20 contacted by the additive components 36 that may have accumulated residue over time can be readily cleaned to avoid potential bacteria buildup.

In the depicted embodiment, discrete openings 142 are provided in the housing 53 for intake air. Further, in the event that there is the ability through repositioning of the gate 94 to substantially, or altogether, block the stream of fluid entrained with droplets generated by the fluid treatment unit 16, the openings 142 allow the air to be diverted therethrough rather than following the aforementioned flow path to and through the volume 24. This affords a pressure relief function and also allows the air with entrained fluid droplets to be diffused into the surrounding space.

Similarly, discrete openings 144 are provided in the wall of the mask body 22. In the event that the user presses his/her face against the surface 26, pressure relief may be afforded by the openings 144, particularly when the user exhales.

In FIGS. 26-30, a modified form of mask is shown at 20". The mask 20" has the same general configuration as the mask 20, described above, and operates in substantially the same manner.

There are two primary differences between the mask 20" and the mask 20. First of all, whereas the lower region at 106 on the mask body 22 has a smooth external surface portion (see FIG. 17) that extends fully around the wall 108 and nests in, to be frictionally maintained within, the housing 53, the corresponding lower region 106" on the mask 20" has a plurality of circumferentially spaced and radially projecting fins 152 that cooperatively perform the holding function of the external surface portion at the lower region 106 of the mask 20. The fins 152 are sufficiently thin that they can readily bend. When the lower region 106" is pressed into the receptacle on the housing 53, the fins 152 are bent and become compressed within the housing 53 as a result of which residual forces are generated in the fins 152 that enhance frictional holding between the mask 20" and the housing 53.

Secondly, the configuration of the wall 108" is different than the wall 108 in terms of defining the receptacles 38 for the additive components 36 and defining the inlet identified generically at 30 in FIG. 1.

The mask 20" has bosses 112", 114", corresponding to the bosses 112, 114. The bosses 112", 114" cooperate to accommodate two of the additive components 36. More specifically, first and second receptacles 38a", 38b" are defined cooperatively by the bosses 112", 114". This receptacle number is not critical.

The exemplary receptacle 38a" is bounded by oppositely opening concave surfaces 154, 156, respectively on the bosses 112", 114". The surfaces 154, 156 are spaced so that the length L (FIG. 23) of the additive component 36 is slightly compressibly captive therebetween.

The wall 108" has openings 130", corresponding to the openings 130 on the mask 20, with the openings 130" having a similar arrangement of rows at 132a", 132b", 132c".

As depicted, the openings 130" all have the same circular shape. This, however, is not a requirement.

The wall 108" and bosses 112", 114" cooperatively define openings 130" corresponding to the openings 130' on the mask 20. The openings 130" are provided in rows 132d''', 132e", at the bosses 112", 114", respectively, and correspond to the opening rows 132d, 132e on the mask 20.

The wall 108" has additional openings 130a" arranged so that there is a more regular pattern of openings to efficiently fill the volume above the wall 108" during operation.

The openings 130" are directly beneath the press fit additive components 36 so that flow through the openings 130" impinges directly upon the operatively positioned additive components 36.

The foregoing disclosure of specific embodiments is intended to be illustrative of the broad concepts comprehended by the invention.

The invention claimed is:

1. A portable air treatment apparatus comprising:
a) an operating unit for producing treated air, the operating unit comprising:
a reservoir for a supply of fluid,
the operating unit configured so that droplets are generated from a fluid in the reservoir,
the operating unit causing generated fluid droplets to be entrained in air and directed in a stream to an outlet for the operating unit;
b) a mask having a body including a peripheral wall extending around a volume and a surface or edge on the peripheral wall at an outlet for the volume to be situated near or against a user's frontal face region with the user's face operatively positioned with respect to the mask,
the mask body further having an inlet in communication with the volume,
the mask and operating unit configured so that the mask can be releasably operatively connected to the operating unit whereby the stream of air with entrained fluid droplets flows through the mask body inlet and into the mask body volume, whereby with the user's face operatively positioned with respect to the mask, at least one of a mouth and nose of the user is situated to inhale the stream of air with entrained fluid droplets in and flowing from the mask body volume; and c) at least one additive component, the at least one additive component and mask configured so that the at least one additive component can be placed in an operative position with respect to the mask wherein the at least one additive component is exposed to the stream of air with entrained fluid droplets flowing into the mask body volume, wherein the mask and at least one additive component in the operative position are movable as a unit relative to the operating unit as the mask is separated from the operating unit, wherein the at least one additive component is in the form of a discrete pad, wherein the mask body has at least one receptacle configured to receive the one additive component with the one additive component in the operative position, wherein the at least one receptacle comprises spaced bosses each comprising an opening, wherein the spaced bosses are configured so that the one additive component can be directed downwardly into openings in the spaced bosses so that the one additive component spans between the spaced bosses with the one additive component in the operative position, wherein the at least one receptacle is within the volume around which the peripheral wall extends so as to be spaced from the peripheral wall.

2. The portable air treatment apparatus according to claim 1 wherein the at least one receptacle is configured to compressibly engage the at least one additive component to thereby maintain the at least one additive component in the operative position in a predetermined relationship with the mask body.

3. The portable air treatment apparatus according to claim 1 wherein the mask body has a wall at which at least a portion of the mask body inlet is located and the at least one receptacle is spaced from the at least portion of the mask body inlet so that the stream of air with entrained fluid droplets moves through the at least portion of the mask body inlet up to, against, and past the at least one additive component, to the volume outlet.

4. The portable air treatment apparatus according to claim 1 wherein the at least one additive component comprises first and second additive components placed in operative positions.

5. The portable air treatment apparatus according to claim 1 wherein the mask body inlet comprises at least one mask body opening beneath the at least one additive component with the at least one additive component in the operative position.

6. The portable air treatment apparatus according to claim 5 wherein the at least mask body one opening comprises a plurality of discrete openings beneath the at least one additive component with the at least one additive component in the operative position, the plurality of discrete openings located so that the stream of air with entrained fluid droplets moves through each of the plurality of discrete openings up to, against, and past the at least one additive component to the volume outlet.

7. The portable air treatment apparatus according to claim 1 wherein the at least one additive component comprises a plurality of additive components each with a flat shape residing in a plane and with the plurality of additive components each in its operative position the planes of the plurality of additive components are substantially parallel.

8. The portable air treatment apparatus according to claim 1 wherein the mask body volume is bounded by a bottom wall and the mask body inlet comprises a plurality of discrete openings in the bottom wall.

9. The portable air treatment apparatus according to claim 1 wherein the at least one receptacle and at least one additive component are configured so that the at least one additive component can be press fit into the at least one receptacle to be releasably maintained in the operative position.

10. The portable air treatment apparatus according to claim 1 wherein the at least one receptacle is located so that the at least one additive component can be directed from a fully separated starting position through the volume outlet and into the operative position.

11. The portable air treatment apparatus according to claim 1 wherein the at least one receptacle and at least one additive component are configured so that the at least one additive component can be press fit into the at least one receptacle and frictionally maintained in the operative position.

12. The portable air treatment apparatus according to claim 1 wherein the at least one additive component has an absorbent body that retains a quantity of a composition that treats the stream of air with entrained fluid droplets as the at least one additive component is exposed to the stream of air with entrained fluid droplets.

13. The portable air treatment apparatus according to claim 1 wherein there are connectors on the mask body and operating unit that cooperate to releasably connect the mask body to the operating unit.

14. The portable air treatment apparatus according to claim 13 wherein the cooperating connectors are configured so that the mask body and operating unit can be relatively moved from a fully separated relationship towards and against each other into a connected relationship and maintained in the connected relationship without requiring use of separate fasteners.

15. The portable air treatment apparatus according to claim 1 wherein the operating unit is configured so that the fluid droplets are generated through one of ultrasonic vibration and heating.

16. The portable air treatment apparatus according to claim 1 wherein the mask body is molded from a pliable material.

17. A portable air treatment apparatus comprising:

a) an operating unit for producing treated air, the operating unit comprising:

a reservoir for a supply of fluid, the operating unit configured so that droplets are generated from a fluid in the reservoir, the operating unit causing generated fluid droplets to be entrained in air and directed in a stream to an outlet for the operating unit;

b) a mask having a body extending around a volume and a surface or edge at an outlet for the volume to be situated near or against a user's frontal face region with the user's face operatively positioned with respect to the mask, the mask body further having an inlet in communication with the volume, the mask and operating unit configured so that the mask can be releasably operatively connected to the operating unit whereby the stream of air with entrained fluid droplets flows through the mask body inlet and into the mask body volume, whereby with the user's face operatively positioned with respect to the mask, at least one of a mouth and nose of the user is situated to inhale the stream of air with entrained fluid droplets in and flowing from the mask body volume; and c) at least one additive component, the at least one additive component and mask configured so that the at least one additive component can be placed in an operative position with respect to the mask wherein the at least one additive component is exposed to the stream of air with entrained fluid droplets flowing into the mask body volume, wherein the mask and at least one additive component in the operative position are movable as a unit relative to the operating unit as the mask is separated from the operating unit, wherein the mask body volume is bounded by a bottom wall and the mask body inlet comprises a plurality of discrete openings in the bottom wall, wherein the mask body has at least one receptacle configured to receive the at least one additive component with the at least one additive component in the operative position and the at least one receptacle comprises spaced seats for the at least one additive component and one of the discrete openings in the bottom wall is located between the spaced seats.

18. A portable air treatment apparatus comprising:

a) an operating unit for producing treated air, the operating unit having a top and bottom and comprising:

a reservoir for a supply of fluid, the operating unit configured so that droplets are generated from a fluid in the reservoir, the operating unit causing generated fluid droplets to be entrained in air and directed in a stream to an outlet for the operating unit;

b) a mask having a body including a peripheral wall extending around a volume and a surface or edge at an outlet for the volume to be situated near or against a user's frontal face region with the user's face operatively positioned with respect to the mask, the mask body further having an inlet in communication with the volume, the mask and operating unit configured so that the mask can be releasably operatively connected to the operating unit whereby the stream of air with entrained fluid droplets flows through the mask body inlet and into the mask body volume, whereby with the user's face operatively positioned with respect to the mask, at least one of a mouth and nose of the user is situated to inhale the stream of air with entrained fluid droplets in and flowing from the mask body volume; and c) at least one additive component, the at least one additive component and mask configured so that the at least one additive component can be placed in at least one receptacle within the mask body volume in an operative position with respect to the mask wherein the at least one additive component is exposed to the stream of air with entrained fluid droplets flowing into the mask body volume, wherein the mask and at least one additive component in the operative position are movable as a unit relative to the operating unit as the mask is separated from the operating unit, wherein the mask body has at least one receptacle configured to receive the at least one additive component and maintain the at least one additive component in a predetermined relationship with the mask with the at least one additive component in the operative position, wherein the at least one additive component comprises a flat shape residing in a plane and with the at least one additive components in its operative position the plane of the at least one additive components extends vertically, wherein the at least one additive component and at least one receptacle are configured so that the at least one additive component can be pressed into, and frictionally maintained within, the at least one receptacle at a location within the mask body volume within the peripheral wall, with the receptacle spaced from the peripheral wall.

19. The portable air treatment apparatus according to claim 18 wherein the at least one receptacle opens upwardly and the at least one receptacle and at least one additive component are configured so that the at least one additive component can be directed downwardly and thereby press fit into the at least one receptacle to be releasably maintained in the operative position.

20. The portable air treatment apparatus according to claim 19 wherein the at least one receptacle and at least one additive component are configured so that the at least one additive component is compressibly deformed and maintained within the at least one receptacle.

21. The portable air treatment apparatus according to claim 18 wherein the at least one additive component comprises a plurality of additive components each with a flat shape residing in a plane and with the plurality of additive components each in its operative position, the planes of the plurality of additive components are substantially parallel and extend vertically.

* * * * *